United States Patent [19]
Ellig et al.

[11] Patent Number: 4,870,223
[45] Date of Patent: Sep. 26, 1989

[54] CATALYTIC PROCESS FOR THE CONVERSION OF HYDROCARBONS

[75] Inventors: Daniel L. Ellig, Des Plaines; George J. Antos, Bartlett, both of Ill.

[73] Assignee: UOP, Des Plaines, Ill.

[21] Appl. No.: 292,148

[22] Filed: Dec. 30, 1988

Related U.S. Application Data

[62] Division of Ser. No. 63,878, Jun. 19, 1987, Pat. No. 4,822,762.

[51] Int. Cl.$^4$ .............................................. C07C 2/52
[52] U.S. Cl. .................................................... 585/419
[58] Field of Search ......................................... 585/419

[56] References Cited

U.S. PATENT DOCUMENTS

| | | | |
|---|---|---|---|
| 4,434,311 | 2/1984 | Buss et al. | 585/444 |
| 4,507,396 | 3/1985 | Hickson | 502/8 |
| 4,582,815 | 4/1986 | Bowes | 502/64 |

Primary Examiner—Curtis R. Davis
Attorney, Agent, or Firm—Thomas K. McBride; John F. Spears, Jr.

[57] ABSTRACT

A nonacidic hydrocarbon conversion catalyst is disclosed which is prepared by incorporating potassium hydroxide into a composite of nonacidic L-zeolite and amorphous silica. A preparation procedure is also disclosed as well as a process for dehydrocyclizing $C_6$ to $C_8$ aliphatic hydrocarbons.

3 Claims, 2 Drawing Sheets

$C_5^+$ Liquid Yield vs. Catalyst Life.

△——△ Catalyst − A
□——□ Catalyst − B

Average Reaction Temperature vs. Catalyst Life.

CATALYTIC PROCESS FOR THE CONVERSION OF HYDROCARBONS

Divisional application of prior copending application Ser. No. 063,878, filed June 19, 1987, now U.S. Pat. No. 4,822,762.

BACKGROUND OF THE INVENTION

The present invention is directed toward a hydrocarbon conversion catalyst which is used especially for effecting the dehydrocyclization of aliphatic hydrocarbons to aromatics. More particularly, the catalyst enables the conversion of $C_6$-plus paraffins to their corresponding aromatics with a high degree of selectivity thereby enabling the facile production of large quantities of aromatics.

In the past, it has become the practice to effect conversion of aliphatic hydrocarbons to aromatics by means of the well-known catalytic reforming process. In catalytic reforming, a hydrocarbonaceous feedstock, typically a petroleum naphtha fraction, is contacted with a Group VIII-containing catalytic composite to produce a product reformate of increased aromatics content. The naphtha fraction is typically a full boiling range fraction having an initial boiling point of from about 10°–38° C. and an end boiling point of from about 107°–218° C. Such a full boiling range naphtha contains significant amounts of $C_6$-plus paraffinic hydrocarbons and $C_6$-plus naphthenic hydrocarbons. As is well known, these paraffinic and naphthenic hydrocarbons are converted to aromatics by means of multifarious reaction mechanisms. These mechanisms include dehydrogenation, dehydrocyclization, and isomerization followed by dehydrogenation. Accordingly, naphthenic hydrocarbons are converted to aromatics by dehydrogenation. Paraffinic hydrocarbons may be converted to the desired aromatics by dehydrocyclization and may also undergo isomerization. Accordingly then, it is apparent that the number of reactions taking place in a catalytic reforming zone are numerous and the typical reforming catalyst must be capable of effecting numerous reactions to be considered usable in a commercially feasible reaction system.

Because of the complexity and number of reaction mechanisms ongoing in catalytic reforming, it has become a recent practice to develop highly specific catalysts tailored to convert only specific reaction species to aromatics. Such catalysts offer advantages over the typical reforming catalyst which must be capable of taking part in numerous reaction mechanisms. Ongoing work has been directed toward producing a catalyst for the conversion of paraffinic hydrocarbons, particularly having six carbon atoms or more, to the corresponding aromatic hydrocarbon. Such a catalyst can be expected to be much more specific resulting in less undesirable side reactions such as hydrocracking. As can be appreciated by those of ordinary skill in the art, increased production of aromatics is desirable. The increased aromatic content of gasolines, a result of lead phase down, as well as demands in the petrochemical industry make $C_6$–$C_8$ aromatics highly desirable products. Accordingly, it would be most advantageous to have a process and a catalytic composition which is highly selective for the conversion of less valuable $C_6$-plus paraffins to the more valuable $C_6$-plus aromatics.

To formulate catalysts capable of effecting the required reactions, it has been increasingly popular to employ crystalline aluminosilicate zeolites in combination with catalytically active metals. A well known method of preparing catalysts containing zeolites is to incorporate the zeolites into refractory inorganic matrices. Primarily, the use of such matrices, sometimes referred to as binders, has typically been directed towards simplification of catalyst manufacture, providing a simple solution to the problem associated with handling the catalytically active microparticles of zeolite. The microparticles of zeolite are combined with the binder to form or shape macroparticles which are then easily handled and utilized, for example, in a chemical reactor. Before or after forming the zeolite/binder composite, various catalytically active metals can be incorporated into the composite depending on the particular reaction to be catalyzed. Although the zeolite and the metals supply the primary catalytic effect, the contribution to the overall catalytic reaction from the binder and the particular method used to form the composite cannot be ignored. Simple changes in formulation, such as, changing from 100% alumina as the binder material to a mixture of alumina and silica can have a dramatic effect on catalytic performance. Likewise, the use of either acidic or basic solutions during preparation of the catalyst can have an effect on the catalytic performance of the finished catalyst. Therefore, with this in mind, broad general teachings relating to catalyst preparation do not typically lead one skilled in the art to design an effective catalyst formulation for specific applications, such as, the reforming of aliphatic hydrocarbons to aromatics.

Of the body of art that relates to the preparation of catalysts containing zeolites, U.S. Pat. No. 4,507,396 does mention that various zeolites, including L-zeolite, can be formed with colloidal inorganic oxide materials, such as, formed silica, to produce solid inorganic bodies. The preparation method disclosed in this reference requires that the zeolite and the colloidal oxide be dispersed in a water-immiscible solvent and then titrated with an aqueous phase to produce a hydrous plastic agglomerate. U.S. Pat. No. 4,434,311 also teaches that L-zeolite can be combined with an inorganic oxide to prepare catalyst particles. In particular, it is mentioned that the L-zeolite can be mixed with a colloidal suspension of silica in water, stabilized with a small amount of alkali, and extruded to form cylindrical pellets. Extrusion aids selected from ethylene glycol and stearic acid may also be employed.

Another reference, U.S. Pat. No. 4,582,815, is believed most germane to the invention disclosed herein. This reference is directed at a preparation method to extrude high silica-containing materials, specifically a class of zeolites belonging to the ZSM family. The method involves the use of an extrusion aid, which is added to the silica-rich material prior to extrusion. Basic salts and hydroxides of the Group I metals are broadly taught as acceptable extrusion aids. However, only one compound is actually named or exemplified, that being sodium hydroxide. After the catalyst is extruded, the extrusion aid is neutralized with an acidic solution and washed from the formed particle prior to the steps of drying and calcination. The washing is performed to avoid entrapment of the sodium cations in the composite. Neutralization with the acidic solution is conducted to reduce the basicity of the composite which is imparted to the composite by the sodium hydroxide. In contradistinction to this reference, the instant invention is directed at not only preserving basicity of an extruded catalyst composite but in addition, incorporating alkali metal cations into the final catalytic composite. Moreover, the '815 patent has not recognized the utility of potassium hydroxide in combination with a nonacidic potassium form type-L zeolite.

OBJECTS AND EMBODIMENTS

It is, therefore, a principal object of the present invention to provide a catalytic compositionfor the conversion of hydrocarbons. A more specific objective is to provide a catalyst for the conversion of $C_6$-plus paraffinic hydrocarbons, especially $C_6$-$C_8$ paraffinic hydrocarbons, to their corresponding aromatics.

Accordingly, a broad embodiment of the present invention is directed toward a hydrocarbon conversion catalyst comprising a platinum component, a nonacidic potassium form L-zeolite, and an amorphous silica binder, where the catalyst is prepared by the steps of: (a) commingling the nonacidic potassium form L-zeolite with an amorphous silica powder; (b) adding an aqueous solution of potassium hydroxide to the L-zeolite and silica powder and mixing to form an extrudable dough; (c) extruding the dough to form extrudates that are nonacidic as a result of the incorporated potassium hydroxide; (d) calcining the extrudates without subjecting the extrudates to any treatment that would neutralize or reduce the basicity of the extrudates or would result in a loss of potassium cations; (e) contacting the calcined extrudate with a solution comprising a platinum component and a potassium componente; and, (f) subjecting the resultant extrudate of step (e) to an oxidation treatment and subsequently to a reduction treatment.

An alternate embodiment of the present invention is a process for the dehydrocyclization of $C_6$-$C_8$ hydrocarbons to aromatics comprising contacting the $C_6$-$C_8$ hydrocarbons in a reaction zone at dehydrocyclization conditions with a catalyst comprising a platinum component, a nonacidic potassium form L-zeolite, and an amorphous silica binder, where the catalyst is prepared by the steps of: (a) commingling the nonacidic potassium form L-zeolite with an amorphous silica powder; (b) adding an aqueous solution of potassium hydroxide to the L-zeolite and silica powder and mixing to form an extrudable dough; (c) extruding the dough to form extrudates that are nonacidic as a result of the incorporated potassium hydroxide; (d) calcining the extrudates without subjecting the extrudates to any treatment that would neutralize or reduce the basicity of the extrudates or would result in a loss of potassium cations; (e) contacting the calcined extrudate with a solution comprising a platinum component and a potassium component; and, (f) subjecting the resultant extrudate of step (e) to an oxidation treatment and subsequently to a reduction treatment.

These as well as other objects and embodiments will become evident from the following, more detaileddescripytion of the present invention.

DETAILED DESCRIPTION OF THE INVENTION

To reiterate briefly, the present invention relates to a hydrocarbon conversion catalyst composition which is formulated in such manner so as to preserve the basicity of the composite which results from using a nonacidic type-L zeolite and the incorporation of potassium hydroxide. The catalyst is especially useful in the dehydrocyclization of aliphatic hydrocarbons to form high yields of aromatic hydrocarbons.

As previously indicated, it is an essential feature of the catalyst of the present invention that it comprise a potassium form nonacidic L-zeolite. By "nonacidic zeolite", it is to be understood that it is meant that the zeolite has substantially all of its cationic sites of exchange occupied by nonhydrogen cationic species. Preferably, such cationic species will comprise the alkali metal cations although other cationic species may be present. Irrespective of the actual type of cationic species present in the sites of exchange, the nonacidic zeolite in the present invention has substantially all of the cationic sites occupied by nonhydrogen cations, thereby rendering the zeolite substantially fully cationic exchanged. Many means are well known in the art for arriving at a substantially fully cationic exchanged zeolite and thus they need not be elaborated herein.

The especially preferred type of nonacidic zeolite of the present invention is L-zeolite. It is required that the cationic exchangeable sites of the L-zeolite be fully cationic exchanged with nonhydrogen cationic species. As also indicated above, typically the cations occupying the cationic exchangeable sites will comprise one or more of the alkali metals including lithium, sodium, potassium, rubidium, and cesium. An especially preferred nonacidic zeolite for application in the present invention is the potassium form of L-zeolite. It should also be understood, however, that the nonacidic L-zeolite of the invention may contain more than one type of the alkali metal cation at the cationic exchangeable sites, for example, sodium and potassium.

In order to allow the L-zeolite to be utilized in a convenient manner, it is necessary to combine it with a binder material. As mentioned above, utilizing a binder material allows for the formation of catalyst particles large enough in size to permit easy commercial handling, typically such particles have diameters of approximately 1/16 of an inch. Although the art teaches that any refractory inorganic oxide binder material will be suitable, we have found that a particular form of amorphous silica when prepared in accordance with the instant invention yields a superior finished catalyst composite. In particular, the preferred amorphous silica is a synthetic, white, amorphous silica (silicon dioxide) powder which is classed as wet-process, hydrated silica. This type of silica is produced by a chemical reaction in a water solution, from which it is precipitated as ultrafine, spherical particles. It is preferred that the BET surface area of the silica is in the range from about 120 to 160 $m^2/g$. A low content of sulfate salts is also desired, preferably less than 0.3 wt.%. Concerning the criterion that the finished catalyst composite be nonacidic, it is preferred that the amorphous silica binder also be nonacidic. The acidic nature of a particular silica can be determined by measuring the pH of a waer suspension of the particular silica in question. It is preferred that the pH of a 5% water suspension be neutral (pH about 7) and most preferably basic (pH greater than 7). A typical pH range for the silica material of the instant invention is 6.5 to 7.3.

The nonacidic potassium form L-zeolite and the amorphous silica powder are commingled to form a uniform powder blend prior to the introduction of a liquid peptizing solution. The weight ratio of L-zeolite to amorphous silica powder can range from about 1:4 to 9:1 based on a water-free weight analysis of both materials. A weight ratio ranging from about 1:1 to about 6:1, on a water-free basis, is most preferred. After the powder blend is prepared, the peptizing agent, which comprises an aqueous solution of potassium hydroxide, is added in sufficient amount that upon mixing, an extrudable dough is formed. An extrudable dough is one that has the correct moisture content to allow for the formation of extrudates that have acceptable integrity to withstand direct calcination. Extrudability is determined from an analysis of the moisture content of the dough. A moisture content in the range of from 30 to 50 wt.% is preferred. The quantity of potassium hydroxide in the peptizing solution is from 0.1 to 1.2 pound of potassium hydroxide per 100 pounds of water-free powder blend, with a preferred range of from about 0.3 to 1.0 pound of potassium hydroxide per 100 pounds of water-free powder blend. Most preferably, the peptizing solution contains about 0.9 pound of potassium hydroxide per 100 pounds of water-free powder blend.

Extrusion of the dough to form an extrudate is performed in accordance with the techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as, spheres, by any means known to the art.

As mentioned, it is critical to the instant invention that the catalyst composite be nonacidic. Thus, it is highly desired that the peptizing agent used be basic, preferably having a pH of greater than 7. By utilizing potassium hydroxide as a peptizing agent, which typically yields a solution pH greater than 10 and incorporating it, into the catalyst formulation, this nonacidity criteria is furthered. Preserving the potassium cations in the extrudate, as well as preserving the basicity imparted to the extrudate by the potassium hydroxide, are essential aspects in the preparation of the catalyst. Thus, in contradistinction to the prior art preparation taught in U.S. Pat. No. 4,582,815, the instant invention does not employ any steps prior to calcination, such as, washing with acid and/or ammonium solutions or replacement of the alkali cations by ion exchange techniques, which would neutralize the basicity of the extrudate imparted by the potassium hydroxide. Moreover, it is a requirement of the instant invention that the extrudates are subject directly to a calcination procedure, without an intermediate drying step. This direct calcination procedure is believed to result in the encapsulation of potassium ions into the catalyst supported thereby preserving the basicity. The calcination of the extrudates is performed in an oxygen-containing atmosphere at a temperature of from about 260° to about 650° C. for a period of about 0.5 to about 2 hours.

A further essential feature of the catalyst of the present invention is the presence of a platinum component. Incorporation of the platinum component may be achieved by any suitable means known in the art. A preferred method incorporates the platinum component after formation of the calcined extrudate. For example, the platinum component may be incorporated with the calcined extrudate by impregnating the extrudate with a solution of dilute chloroplatinic acid or by ion exchanging the potassium cations of the L-zeolite with a solution of tetra-amine platinum chloride. Regardless of the means chosen, it is preferred that a potassium component is included with the solution containing the platinum component. Any potassium compound or mixtures of potassium compounds that will readily dissociate in a particular solvent chosen can be utilized, such as, potassium chloride, potassium citrate, potassium acetate, potassium carbonate, potassium bicarbonate, and the like. An ion exchange procedure using a solution comprising tetra-amine platinum chloride and potassium chloride is the preferred procedure for incorporating the platinum with the catalyst. The amount of platinum component added to the catalyst is from about 0.01 to about 5 wt.% based on the total weight of the finished catalyst, with a most preferred platinum content of from 0.5 to 2 wt.%.

Regardless of the details of how the platinum component of the catalyst is combined with the L-zeolite and amorphous silica binder, the final catalyst generally will be dried at a temperature of about 93° to about 316° C. for a period of from about 0.5 to about 24 hours or more, and finally oxidized at a temperature of about 316° to about 550° C. in an air atmosphere, preferably at 350° C., for a period of about 0.5 to about 10 hours. After the oxidation step, it is preferred that the catalyst be subjected to a substantially water-free reduction step prior to its use in the conversion of hydrocarbons. This step is designed to ensure a uniform and finely divided dispersion of the platinum component throughout the nonacidic potassium form L-zeolite. Preferably, substantially pure and dry hydrogen (i.e., less than 20 vol. ppm $H_2O$) is used as the reducing agent in this step. The reducing agent is contacted with the oxidized catalyst at a temperature of about 300° to about 550° C., preferably at 350° C., and for a period of time of about 0.5 to 10 hours or more, effective to reduce substantially all of the platinum component. It is preferred that the contact time in the reducing atmosphere be no longer than necessary in order to avoid any pre-deactivation of the catalyst which may occur. This pre-deactivation of the catalyst would show up as lower than expected activity performance when the catalyst was used in a hydrocarbon conversion process. This reduction treatment may be performed in situ as part of a startup sequence if precautions are taken to predry the plant to a substantially water-free state and if substantially water-free hydrogen is used.

In addition to comprising a platinum component, it is contemplated in the present invention that the catalyst thereof may contain other metal components well known to have catalyst modifying properties. Such metal components include rhenium, iridium, tin, cobalt, indium, gallium, lead, zinc, uranium, thallium, dysprosium, germanium, etc. Incorporation of such metal components as promoters and/or extenders has proven beneficial in catalyst reforming. Accordingly, it is within the scope of the present invention that catalytically effective amounts of such modifiers may be beneficially incorporated into the catalyst of the present invention improving its performance.

As previously indicated, the catalytic composite of the present invention has particular utility as a hydrocarbon conversion catalyst. Accordingly, a hydrocarbon charge stock is contacted a hydrocarbon conversion conditions with the catalytic composite of the present invention. A wide range of hydrocarbon conversion conditions may be employed and the exact conditions will depend upon the particular charge stock and reaction to be effected. Generally, these conditions include a temperature of about 260°–815° C., a pressure of from about 101 kPa (abs) to about 3500 kPa (ga), a liquid hourly space velocity (calculated on the basis of equivalent liquid volume of the charge stock contacted with the catalyst per hour divided by the volume of conversion zone containing catalyst) of about 0.2 to 15 $hr^{-1}$.

Furthermore, hydrocarbon conversion conditions may include the presence of diluent such as hydrogen. When such is the case, the hydrogen to hydrocarbon mole ratio may be from about 0.5:1 to about 30:1.

The instant invention, as mentioned above, also involves the process of converting a hydrocarbon charge stock at catalytic dehydrocyclization conditions. In particular, the preferred hydrocarbon charge stock comprises $C_6$-$C_8$ nonaromatic hydrocarbons. Accordingly, the present invention involves contacting a hydrocarbon charge stock comprising $C_6$-$C_8$ nonaromatic hydrocarbons with the catalyst described hereinabove at dehydrocyclization conditions. Dehydrocyclization conditions include a pressure of from about 101 to about 4137 kPa (ga), with the preferred pressure being from about 172 to about 1379 kPa (ga), a temperature of from about 350° to 650° C., and a liquid hourly space velocity of from about 0.1 to about $10^{-1}$. Preferably, hydrogen may be employed as a diluent. When present, hydrogen may be circulated at a rate of from about 0.2 to about 10 molee of hydrogen per mole of charge stock hydrocarbon.

In accordance with the present invention, a hydrocarbon charge stock is contacted with the catalytst in a hydrocarbon conversion zone. This contacting may be accomplished by using the catalyst in a fixed-bed system, a moving-bed system, a fluidized-bed system, or in a batch-type operation. The hydrocarbon charge stock and, if desired, a hydrogen-rich gas as diluent are typically preheated by any suitable heating means to the desired reaction temperature and then are passed into a conversion zone containing the catalyst of the invention. It is, of course, understood that the conversion zone may be one or more separate reactors with suitable means therebetween to ensure that the desired conversion temperature is maintained at the entrance to each reactor. It is also important to know that the reactants may be contacted with the catalyst bed in either upward, downward, or radial-flow fashion. When the final shape of the catalyst is spherical, the latter method is preferred. In addition, the reactants may be in the liquid phase, a mixed liquid-vapor phase, or a vapor phase when they contact the catalyst. Best results are obtained when the reactants are in the vapor phase.

After contact with the ctalyst, the hydrocarbon charge stock having undergone dehydrocyclization is withdrawn as an effluent stream from the reaction zone and passed through a cooling means to a separation zone. In the separation zone, the effluent may be separated into various constituents depending upon the desired products. When hydrogen is utilized as a diluent in the reaction zone, the separation zone will typically comprise a vapor-liquid equilibrium separation zone and a fractionation zone. A hydrogen-rich gas is separated from a high octane liquid product containing aromatics generated within the dehydrocyclization zone. After separation, at least a portion of the hydrogen-rich gas may be recycled back to the reaction zone as diluent. The balance of the hydrogen-rich gas may be recovered for use elsewhere. The high octane liquid product comprising aromatics may then be passed to a fractionation zone to separate aromatics from the unconverted constituents of the charge stock. Alternatively, the liquid product may be passed to either a solvent extraction process or molecular sieve separation process to accomplish the separation of aromatics from unconverted materials. These unconverted constituents may then be passed back to the reaction zone for processing or to other processes for utilization elsewhere.

A wide range of hydrocarbon charge stocks may be employed in the process of the present invention. The exact charge stock utilized will, of course, depend on the precise use of the catalyst. Typically, hydrocarbon charge stocks which may be used in the present invention will contain naphthenes and paraffins, although in some cases, aromatics and olefins may be present. Accordingly, the class of charge stocks which may be utilized includes straight-run naphthas, natural naphthas, synthetic naphthas, and the like. Alternatively, straight-run and cracked naphthas, may also be used to advantage. The naphtha charge stock may be a full-boiling range naphtha having an initial boiling point of from about 10°-70° C. and an end boiling point within the range of from about 163°-218° C., or may be a selected fraction thereof. Generally, any feed rich in paraffinic hydrocarbons will be applicable, preferably those with a low percentage of branched paraffins, such as, raffinates from aromatic extraction process or extracts from molecular sieve separation processes. These highly paraffinic feeds have an end boiling point within the range of from about 95° to 115° C. It is preferred that the charge stocks employed in the present invention be treated by conventional catalytic pretreatment methods such as hydrorefining, hydrotreating, hydrodesulfurization, etc., to remove substantially all sulfurous, nitrogenous, and water-yielding contaminants therefrom. Alternatively, feed pretreatment may be accomplished by non-hydroprocessing methods, such as, contacting with non-catalytic adsorbents, molecular sieves, activated carbons, high-surface area aluminas, and high surfacearea sodium driers.

It is preferred that the charge stock of the instant invention substantially comprise paraffins. This, of course, is a result of the fact that the purpose of a dehydrocyclization process is to convert paraffins to aromatics. Because of the value of $C_6$-$C_8$ aromatics, it is additionally preferred that the hydrocarbon charge stock comprise $C_6$-$C_8$ paraffins. However, notwithstanding this preference, the hydrocarbon charge stock may coprise naphthenes, aromatics, and olefins in addition to $C_6$-$C_8$ paraffins.

In order to more fully demonstrate the attendant advantages arising from the present invention, the following examples are set forth. It is to be understood that the following is by way of example only and is not intended as an undue limitation on the otherwise broad scope of the present invention.

It should be understood that there are three parameters useful in evaluating hydrocarbon conversion process and catalyst performance, and in particular in evaluating and comparing dehydrocyclization catalysts. The first is "activity" which is a measure of the catalyst's ability to convert reactants at a specified set of reaction conditions. The second catalyst performance criteria is "selectivity" which is an indication of the catalyst's ability to produce a high yield of the desired product. The third parameter is "stability" which is a measure of the catalyst's ability to maintain its activity and selectivity over time. In the appended examples, the criterion which will be of interest is catalyst selectivity. For purposes of the following, the catalyst of the invention is exemplified as a dehydrocyclization catalyst and the measure of catalyst selectivity is the production of aromatics and $C_5+$ liquid products. Also indicative of a highly selective catalyst is a low production of light hydrocarbons, namely, $C_1$ to $C_4$ hydrocarbons.

BRIEF DESCRIPTION OF THE DRAWINGS

Each of the drawings described below shows the performance data for Catalyst A made in accordance with the invention as compared to data for Catalyst B not made in accordance with the invention.

EXAMPLE I

Figure 1:
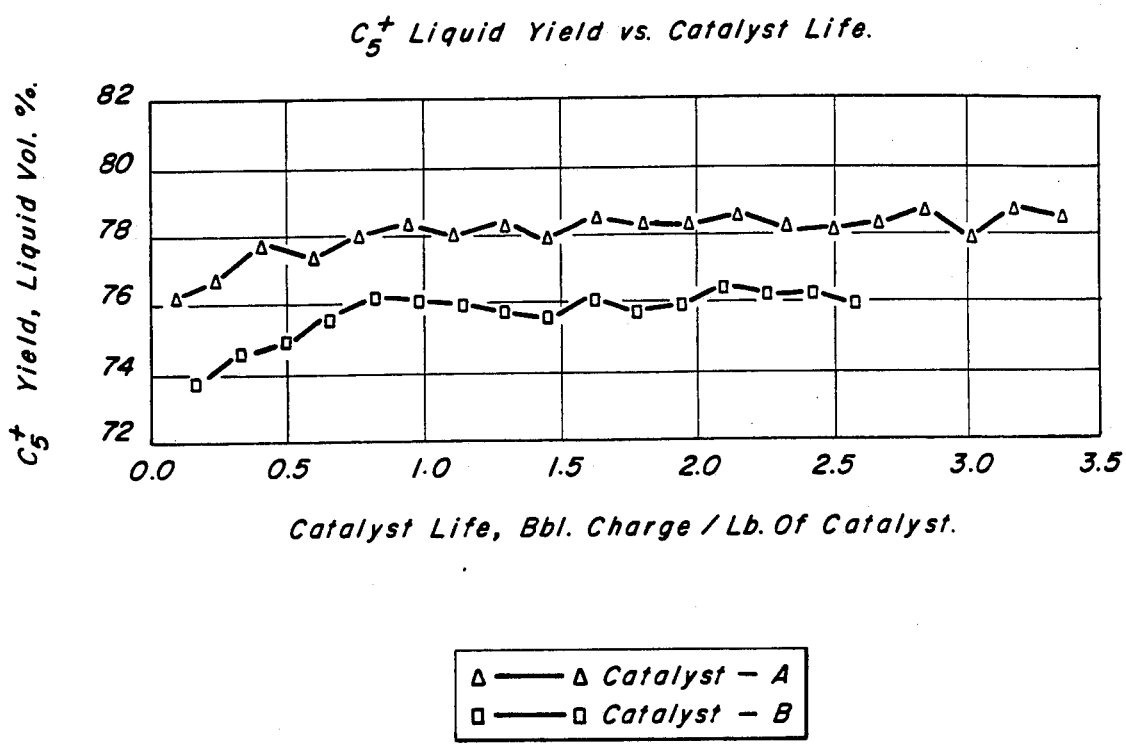
FIG. 1 is a graphical depiction of catalyst selectivity as measured by the volume percent yield of $C_5+$ hydrocarbons as a function of catalyst life measured in barrels of charge stock processed per pound of catalyst.

A first catalyst was made in accordance with the invention. Nonacidic potassium form L-zeolite was blended at about a 6:1 weight ratio (water-free basis) with hydrated amorphous silica powder, Hil-Sil 250 manufactured by PPG. This powder blend was fed continuously to a mixer along with a 10 wt.% aqueous potassium hydroxide peptizing solution and a sufficient amount of water to achieve an extrudable dough having a moisture content of about 40 wt.%. The rate of addition of the potassium hydroxide peptizing solution was set to equal about 0.9 pound of potassium hydroxide per 100 pounds of powder blend (water-free basis). The dough was then extruded through a 1/16-inch die to form cylindrical extrudates. These extrudates were directly subjected to a calcination procedure without any prior washing or drying treatments. Calcination of the extrudates occurred in flowing air for a period of 75 minutes at a temperature of 571° C.

The calcined extrudates were then subjected to an ion exchange procedure using a solution of tetra-amine platinum chloride and potassium chloride. Upon completion of the ion exchange, the catalyst was dried, oxidized, and reduced to yielda catalyst containing 0.69 wt.% platinum and 14.6 wt.% potassium oxide. This catalyst was designated as Catalyst A.

EXAMPLE II

A second catalyst, not made in accordance with the invention, was prepared and evaluated in order to compare a catalyst having less basicity than the catalyst of the instant invention. This catalyst was designated as Catalyst B and was formulated in an identical manner as Catalyst A of Example I except that deionized water was used instead of potassium hydroxide as the peptizing agent. Catalyst B contained about 0.93 wt.% platinum and 14.0 wt.% potassium oxide.

EXAMPLE III

Catalysts A and B were each subjected to a test to measure their respective performance as dehydrocyclization catalysts. The results of the tests are set forth in FIGS. 1, 2, 3, and 4.

The charge stock utilized in each test of this example had the following analysis:

| | |
|---|---|
| $C_3/C_4/C_5$ paraffins | 0.4 wt. % |
| $C_6$ paraffins | 44.3 wt. % |
| $C_6$ naphthenes | 3.1 wt. % |
| $C_7$ paraffins | 44.4 wt. % |
| $C_7$ naphthenes | 1.9 wt. % |
| $C_8$ paraffins | 1.6 wt. % |
| $A_6$ | 0.3 wt. % |
| $A_7$ | 1.1 wt. % |
| olefins | 2.9 wt. % |

The tests were run in a pilot plant having a reactor in which the catalyst to be tested was emplaced. The reactor effluent was analyzed by means of standard gas chromatograph techniques.

The conditions employed during testing of the catalysts were a 1.5 $hr^{-1}$ liquid hourly space velocity and a reaction zone pressure of 414 kPa (ga). Reaction temperature was constantly increased throughout the test to maintain a research octane of the product of 99 RONC. Hydrogen was admixed with the charge stock prior to contact with the catalysts. Sufficient hydrogen on a recycle basis was used to provide a 5:1 ratio of moles of hydrogen to moles of hydrocarbon charge stock.

Figure 2:
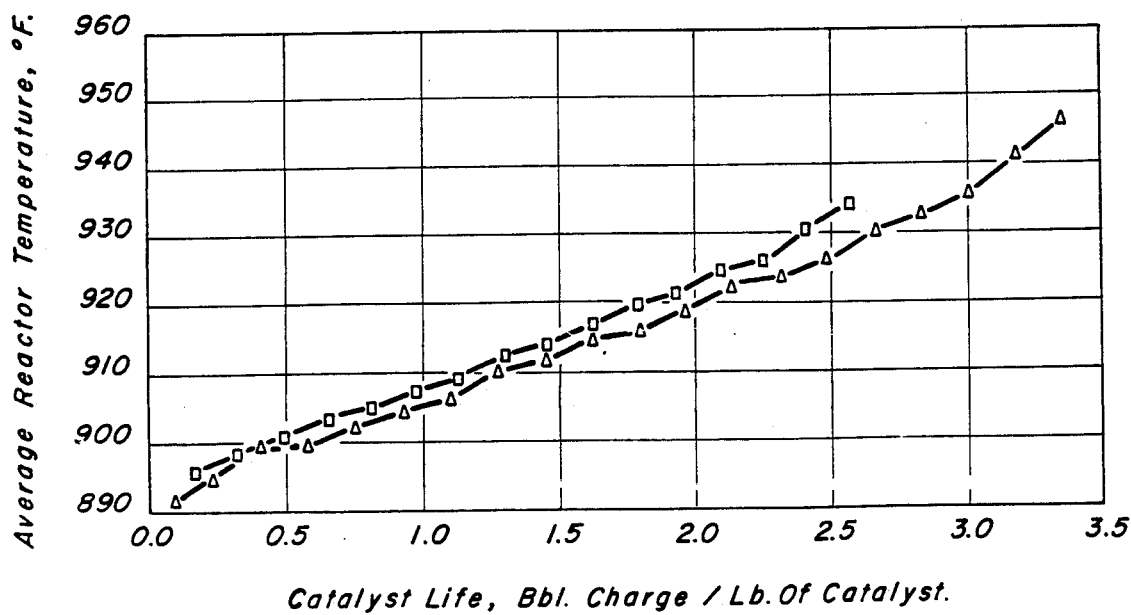
FIG. 2 is a graphical depiction of catalyst activity as measured by average reaction zone temperature necessary to provide a reformate of 99 research octane number as a function of catalyst life measured in barrels of charge stock processed per pound of catalyst.
Figure 3:
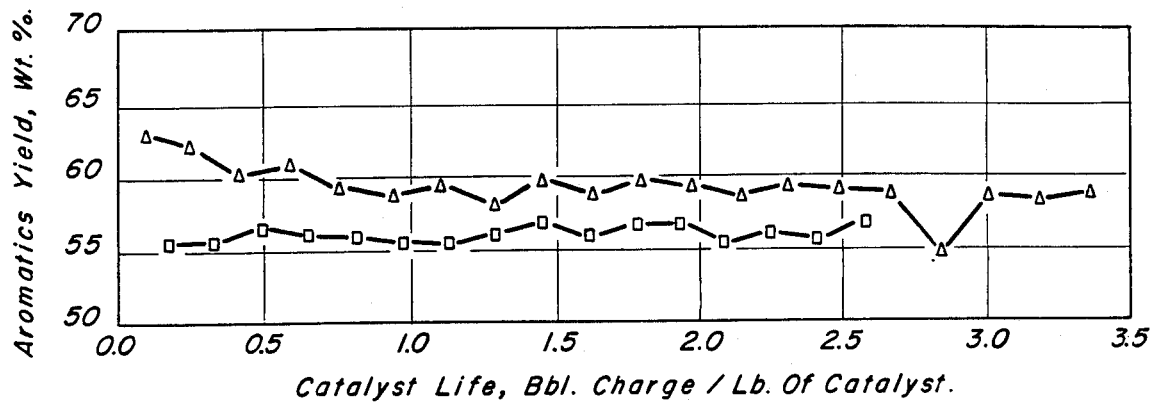
FIG. 3 is a graphical depiction of catalyst selectivity as measured by the weight percent production of aromatic compounds as a function of catalyst life measured in barrels of charge stock processed per pound of catalyst.
Figure 4:
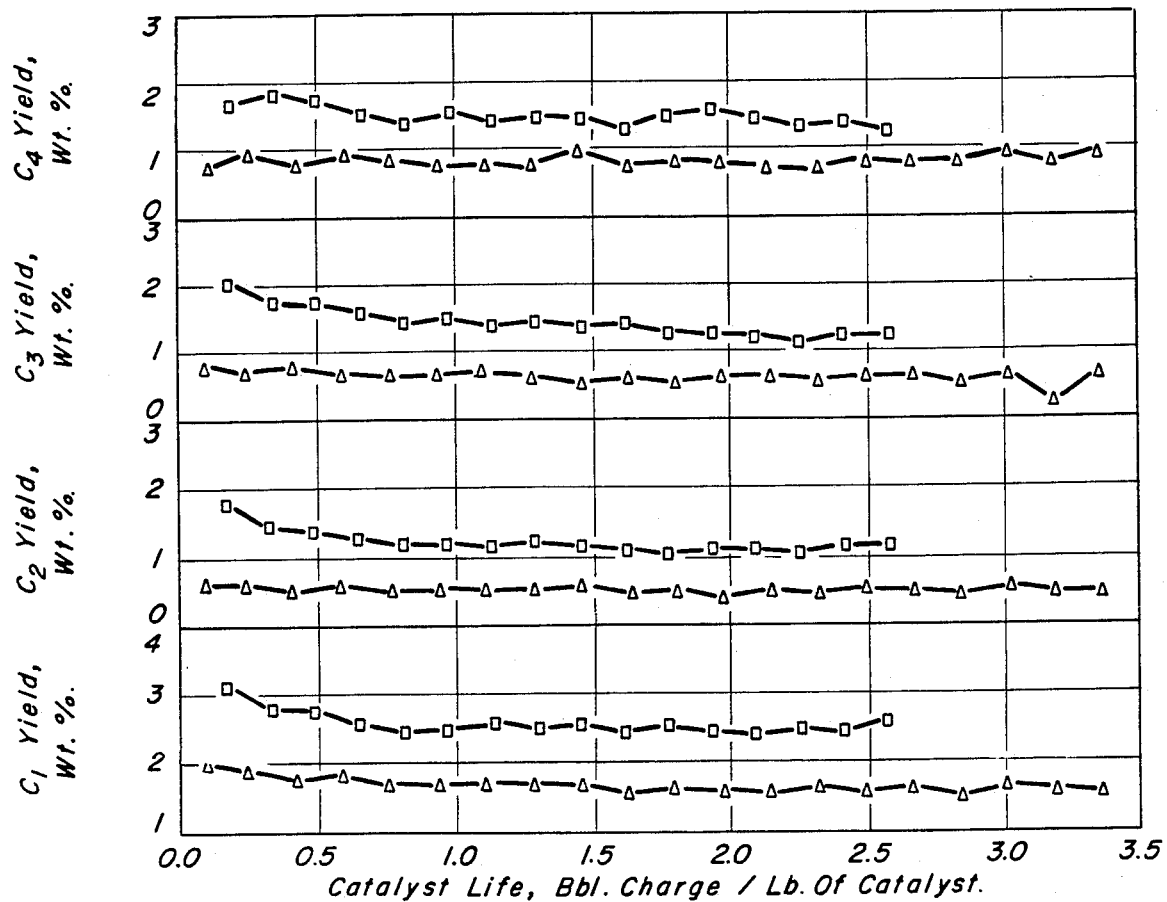
FIG. 4 is a graphical depiction of catalyst selectivity as measured by the weight percent production of light hydrocarbons, $C_1$ to $C_4$, as a function of catalyst life measured in barrel of charge stock processed per pound of catalyst.

Results from the test runs are set forth in FIGS. 1, 2, 3, and 4. FIG. 1 clearly shows the yield advantage exhibited by Catalyst A, averaging about 2 wt.% higher $C_5+$ liquid yield throughout the run. FIG. 2 shows a slight start of run activity advantage for Catalyst A and a slight activity stability advantage compared to Catalyst B. FIG. 3 shows a 3 wt.% higher aromatic yield for Catalyst A and FIG. 4 graphically illustrates the non-acidic nature of Catalyst A which is evidenced by significantly lower yields of light hydrocarbon by-products.

What is claimed is:

1. A process for the dehydrocyclization of $C_6-C_8$ hydrocarbons to aromatics comprising contacting the $C_6-C_8$ hydrocarbons in a reaction zone at dehydrocyclization conditions with a catalyst comprising a platinum component, a non-acidic potassium form L-zeolite and an amorphous silica binder, where the catalyst is prepared by the steps of:

(a) commingling the non-acidic potassium form L-zeolite with an amorphous silica powder;

(b) adding an aqueous solution of potassium hydroxide to the L-zeolite and silica powder and mixing to form an extrudable dough;

(c) extruding the dough to form extrudates that are non-acidic as a result of the incorporated potassium hydroxide;

(d) calcining the extrudates at temperatures exceeding 260° C. without prior washing or low-temperature drying of the extrudates or without subjecting the extrudates to any treatment that would neutralize or reduce the basicity of the extrudates or would result in a loss of potassium cations;

(e) contacting the calcined extrudate with a solution comprising a platinum component and a potassium component; and,
(f) subjecting the resultant extrudate of step (e) to an oxidation treatment and subsequently to a reduction treatment.

2. The process of claim 1 further characterized in that the $C_6$–$C_8$ hydrocarbons are substantially paraffinic.

3. The process of claim 1 further characterized in that the dehydrocyclization conditions comprise a temperature of from about 350° to about 650° C., a reaction pressure of from about 101 to about 4137 kPa (ga), a liquid hourly space velocity of from 0.1 to about 10 $hr^{-1}$, and a hydrogen to $C_6$–$C_8$ hydrocarbon feed mole ratio from about 0.2 to about 10.

* * * * *